United States Patent
Tydings et al.

(10) Patent No.: US 6,379,620 B1
(45) Date of Patent: Apr. 30, 2002

(54) ASSAYING DEVICE AND METHOD FOR IN FIELD URINALYSIS

(76) Inventors: Barry M. Tydings, 1661 Devonshire Ct., Westlake Village, CA (US) 91361; James P. Lee, 2774 Loker Ave. West, Carlsbad, CA (US) 92008

( * ) Notice: Subject to any disclaimer, the term of this patent is extended or adjusted under 35 U.S.C. 154(b) by 0 days.

(21) Appl. No.: 09/192,969

(22) Filed: Nov. 16, 1998

(51) Int. Cl.[7] .................. G01N 31/22; G01N 33/50; G01N 21/78
(52) U.S. Cl. ............... 422/58; 422/50; 422/56; 422/60; 422/61; 422/102; 436/164; 436/169; 436/170; 436/180
(58) Field of Search ............... 422/56, 58, 60, 422/61, 102; 436/164, 169, 170, 180

(56) References Cited

U.S. PATENT DOCUMENTS

| | | | | |
|---|---|---|---|---|
| 4,624,929 A | * | 11/1986 | Ullman | 436/179 |
| 5,119,830 A | * | 6/1992 | Davis | 128/771 |
| 5,186,897 A | * | 2/1993 | Eason et al. | 422/100 |
| 5,403,551 A | | 4/1995 | Galloway et al. | |
| 5,409,664 A | * | 4/1995 | Allen | 422/56 |

* cited by examiner

Primary Examiner—Jill Warden
Assistant Examiner—Latoya I. Cross
(74) Attorney, Agent, or Firm—Koda & Androlia

(57) ABSTRACT

An assay device for in field urine analysis including a container having an opening for collecting a urine sample, a cover for sealing the opening of the container and an assay assembly provided in the container for chemically analyzing the urine sample. The assay assembly comprises a liquid impermeable backing, a wicking material provided on a rear surface of the backing, at least one assay strip provided on a front surface of the backing and adjacent a top edge of the backing in contact with the wicking material, a front cover provided on the front surface of the backing for sealing the assay strip to the backing at a bottom and two sides of the assay strip and a rear cover provided on the rear surface of the backing for together with the front cover sealing said wicking material and the assay strip adjacent the top edge and two sides of said wicking material.

6 Claims, 2 Drawing Sheets

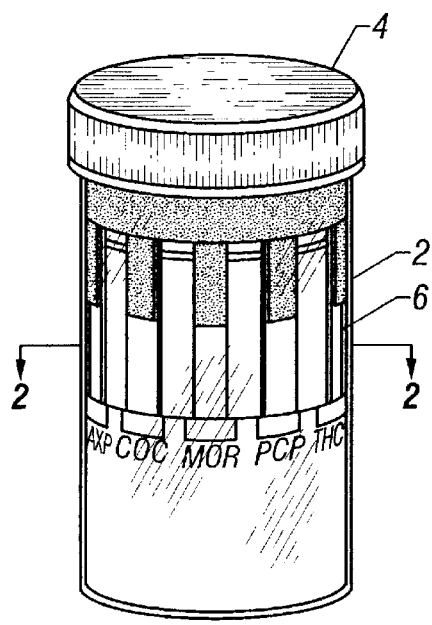
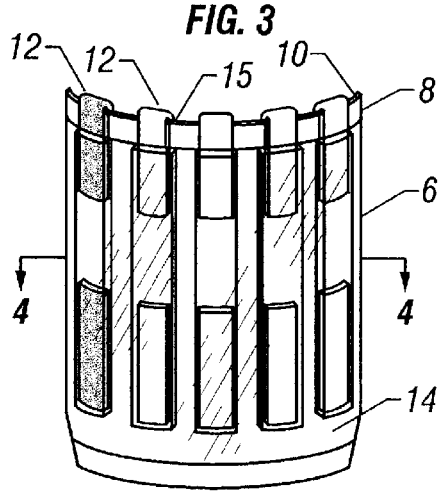
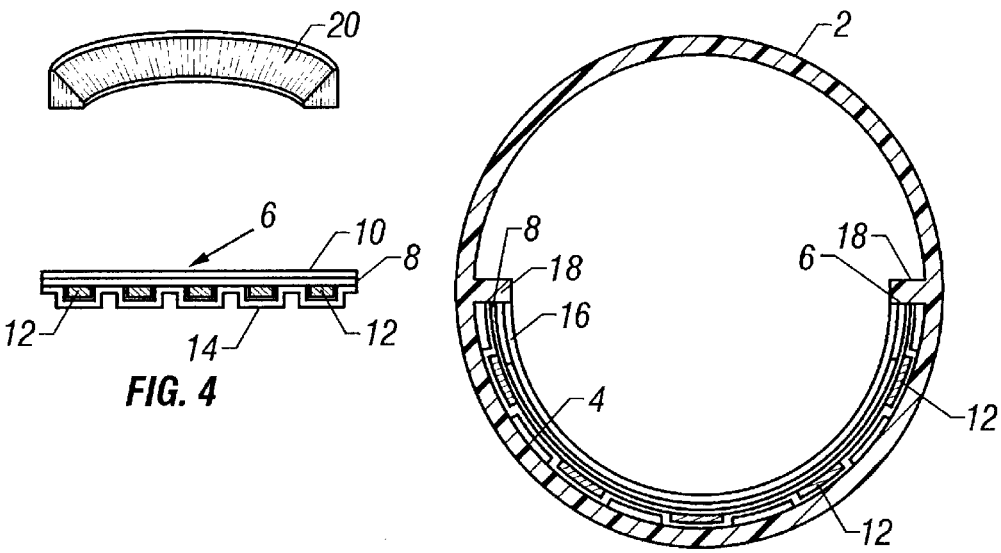

ASSAYING DEVICE AND METHOD FOR IN FIELD URINALYSIS

BACKGROUND OF THE INVENTION

1. Field of the Invention

This invention relates to assaying devices and particularly to assaying devices suitable for use in the field for determining the presence of undesirable chemical constituents or diseases.

2. Prior Art

With the increasing availability and use of drugs by the general population, employers such as government agencies, sports groups and transportation related companies utilize drug screenings as both conditions of employment and maintenance of safety in the workplace. To have a doctor present at the workplace to perform the drug screenings is both expensive and impractical for an employer. Accordingly, other methods have been developed to perform the drug screenings.

One such prior art method is shown in U.S. Pat. No. 5,403,551 entitled "Assaying Device and Container for In Field Analysis of a Specimen and Later Shipment of the Unadulterated Specimen." This device is supposed to be designed to be utilized in field by laymen; however, it is relatively expensive to manufacture because it requires special components, and particularly a special cup, and is relatively complex to operate by laymen and is subject to leakage and contamination.

SUMMARY OF THE INVENTION

Accordingly, it is a general object of the present invention to provide an assaying device which overcomes the disadvantages of the prior art.

In particular, it is a general object of the present invention to provide an assaying device which is capable of easily collecting and testing a urine sample while maintaining the urine sample unadulterated and secure.

It is still another object of the present invention to provide an assaying device which can be used in the field which is simple to use and inexpensive and easy to manufacture.

In keeping with the principles of the present invention, the objects are accomplished by an assaying device for in field urine analysis which includes a container having an opening for collecting a urine sample, a cover for sealing the opening of the container and an assay assembly provided in the container for chemically analyzing the urine sample. The assay assembly includes a liquid impermeable backing, a wicking means provided on a rear surface of said backing, at least one assay strip provided on a front side of the backing and extending over a top edge of the backing and overlaying the wicking material, a front cover provided on the front side of the backing for sealing the assay strip to the backing at the bottom and two sides of the assay strip and a rear cover provided on the rear of the backing for together with the front cover sealing the wicking material and the overlaying assay strip at a top and two sides of the wicking material.

BRIEF DESCRIPTION OF THE DRAWINGS

The above-mentioned features and objects of the present invention will become more apparent with reference to the following description taken in conjunction with the accompanying drawings wherein like reference numerals denote like elements and in which:

FIG. 1 is a side view of an assay device in accordance with the teachings of the present invention;

FIG. 2 is a cross-sectional view of a first embodiment of an assay device in accordance with the teachings of the present invention taken along the lines 2—2 in FIG. 1;

FIG. 3 is a front view of a first embodiment of an assay means in accordance with the teachings of the present invention;

FIG. 4 is a cross-section of FIG. 3 along the lines 4—4 of FIG. 3;

FIG. 5 is a view of a partial retaining ring utilized in a first embodiment of an assay device in accordance with the teachings of the present invention;

DETAILED DESCRIPTION OF THE INVENTION

Figure 6:
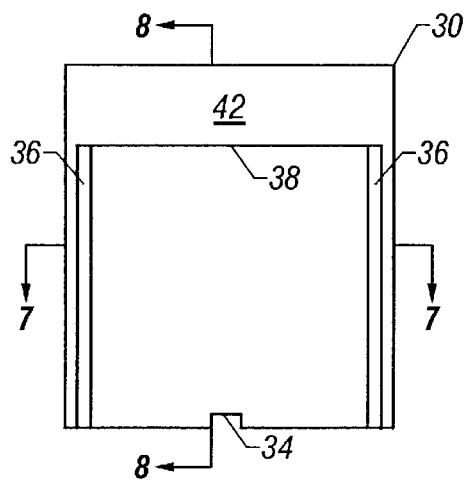
FIG. 6 is a front view of a portion of an assay means in accordance with a second embodiment of the present invention.
Figure 7:
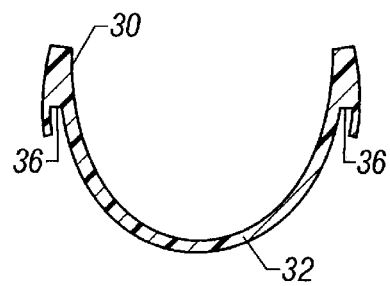
FIG. 7 is a cross-sectional view of FIG. 6 along the lines 7—7 in FIG. 6.
Figure 8:
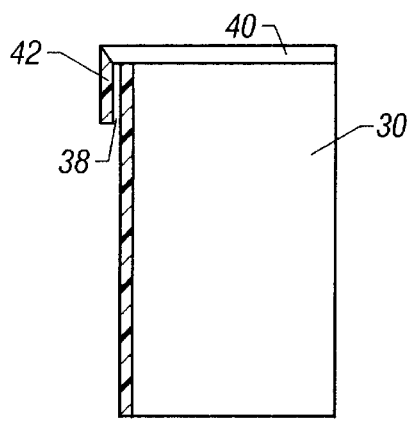
FIG. 8 is a cross-sectional view of FIG. 6 along the lines 8–8 in FIG. 6.

Referring to FIGS. 1–5, shown therein is a first embodiment of an assay device in accordance with the teachings of the present invention. The assay device generally includes a container 2 with a screw lid 4 for closing the open end of the container 2. Inside of the container 2 is provided an assay means 6 such as is shown in FIG. 3. The assay means 6 is installed within the container 2 as is shown in FIG. 2.

In particular, the assay device 6 comprises a backing 8 which is made from a resilient, liquid impermeable material. Typically one such material would be a plastic which is not reactive with any of the components of urine. On the rear side of the backing 8 is provided a wicking material 10. The wicking material 10 extends substantially the full length of the backing 8 and can be made of any material which will wick up a liquid such as filter paper, unwoven papers, fiber glass, etc.

Assay strips 12 are provided on a front surface of the backing 8. These assay strips 12 are for the purpose of chemically analyzing the urine sample to see if it contains any drugs such as amphetamines, cocaine, morphine, PCP, THC and/or their metabolites. To test for these drugs, the assay strips 12 each contain a reagent which is well known in the art for detecting an appropriate drug. Such reagents include, but are not limited to, colloidal gold coated sheep polyclonal anti-amphetamine, mouse monoclonal anti-benzoyl ecgonine, polyclonal rabbit anti-morphine-3 glucuronide, mouse monoclonal anti-cannabinoid or mouse monoclonal anti-phencyclidine, appropriate drug or drug analog conjugates, and immobilized antisera.

The front surface of the backing 8 is covered by a front cover 14 which seals the assay strips 12 at the bottom and both sides of each assay strips 12 so as to isolate each assay strip 12 from each other and prevent contamination from either the urine or another assay strip 12. The front cover 14 is sealed to the backing 8 by a suitable adhesive or other means such as ultrasonic or heat welding. The top portion of the reagent strip 12 is bent over the top edge 15 of the backing 8 and overlapped onto the wicking paper 10.

Alternatively, the wicking material 10 can be folded over the top edge 15 and overlapped onto the assay strips 12. The assay device 6 together with a rear cover 16 are inserted into the container 2 as shown in FIG. 2. The container 2 is provided with longitudinally extending tabs 18 which help hold the assay means 6 in place in the container 2. A partial snap ring 20 as shown in FIG. 5 is then inserted into the container 2 above the assay means 6 and between the tabs 18 to hold the assay means 6 in place and to prevent urine from entering the assay means from the top.

In actual construction, the assay means 6 is substantially the same height in the longitudinal direction as the container 2 with the rear cover 16 being slightly shorter so as to leave a small gap between the bottom of the container 2 and the bottom end of the rear cover 16. Also, it is preferred that the container 2 and front cover 14 be made from transparent plastic.

In operation, the cap 4 is unscrewed from the container 2. A urine sample is then introduced into the container 2. The urine sample need only be minimum in volume and only needs to be deep enough to cover the gap between the bottom of the container 2 and the bottom end of the rear cover 16. As soon as the urine sample is introduced, the cap 4 should be tightly screwed onto the container 2 to prevent any contamination of the urine sample. The urine then wicks up the wicking material 10 until it reaches the overlapped portions of the assay strips 12. The urine then wicks over the top edge of the backing 8 and down the assay strips 12. The urine wicking down the assay strips 12 will react with the chemical agents contained therein and will give positive, negative or inconclusive test results. If the results are positive, the container can then be sealed with an evidence tape and sent to a certified laboratory for confirmation of the in field test results without contaminating or adulterating the urine sample contained within the container 2.

Figure 9:
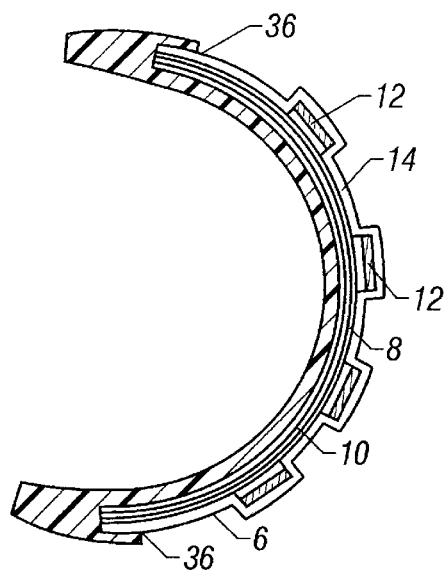
FIG. 9 is a cross-sectional view similar to that of FIG. 2 illustrating a completed assay assembly in accordance with a second embodiment of the present invention ready for installation into the container of the assay device.

Referring to FIGS. 6, 7, 8, and 9, shown therein is a second embodiment of the assay device of the present invention. In particular, shown in the FIGS. 6–9 is essentially an injection molded rear cover 30 for holding the assay means 6 comprising the front cover 14, backing 8, wicking material 10 and assay strips 12. The injection molded rear cover 30 is substantially the same height as the inside of the container 2, is injection molded from a suitable resilient plastic and is provided at the bottom of the front of the curved portion 32 with a cut-out 34. Both sides of the curved portion 32 are further provided with vertically extending slots 36 and a horizontally extending slot 38 as is shown in the FIGS. 7 and 8. The inside top portion of the injection molded rear cover 30 is provided with a beveled edge 40 to assist in the guiding of the urine sample into the inside of the container 2 and further prevent contamination of the assay means 6. As can be seen in FIG. 9, the assay means 6 is assembled to the injection molded rear cover 30 by means of inserting it into the vertical slots 36 and horizontal slot 38. This assembled piece is then placed inside of the container 2 and the cap 4 screwed thereon. In some constructions, it may be desirable to first apply a suitable adhesive to a portion of the upper horizontally extending surface 42 of the rear cover 30. Also, to reduce the cost of manufacture, a container without tabs 18 can be used.

The operation of this second embodiment is substantially the same as the first. In particular, the cap 4 is first removed from the container 2. A urine sample is then provided into the container 2 and the cap 4 is screwed back onto the container 2. The urine sample propagates through the slot 34 and wicks up through the wicking material 10 until it reaches the assay strips 12. The urine sample then wicks over the top of the backing 8 and down the assay strips 12 to activate the various chemical reagents to test for various drugs.

It should also be apparent that while the present invention has been described in terms of testing for drugs, it could be modified by utilizing other reagents and chemicals on the assay strips to test for anything which might be present in the urine. It could be utilized to test for sugar, uric acid, ammonia, alcohol and other sexually transmitted diseases such as clomedia.

It should be apparent to those skilled in the art that the above-described embodiments are merely illustrative of but a few of the embodiments which could be created by one of ordinary skill in the art without departing from the spirit and scope of the present invention.

We claim:

1. An assaying device for in field urine analysis comprising:
   a transparent container means having an opening for collecting a urine sample;
   a cover means for sealing said opening of said container means; and
   an assay assembly provided in said container means for chemically analyzing said urine sample, said assay assembly comprising;
   a liquid impermeable backing;
   at least one assay strip provided on a front surface of said liquid impermeable backing facing outwardly and viewable through said transparent container means;
   a wicking means provided on a rear surface of said liquid impermeable backing separated from said assay strip by said liquid impermeable backing with one portion of said wicking means extending over a top edge of said liquid impermeable backing and overlapping a top portion of said assay strip;
   a front cover means provided on said front surface of said liquid impermeable backing, said front cover means sealing said assay strip to said liquid impermeable backing at a bottom and two sides of said assay strip; and
   a rear cover means provided on said rear surface of said liquid impermeable backing for sealing said wicking means to said liquid impermeable backing at two sides of said wicking means.

2. An assay assembly for chemically analyzing a urine sample, said assay assembly comprising:
   a liquid impermeable backing;
   at least one assay strip provided on a front surface of said liquid impermeable backing;
   a wicking means provided on a rear surface of said backing with one portion of said wicking means extending over a top edge of said liquid impermeable backing with said portion of said wicking means overlapping a top portion of said assay strip;
   a front cover means provided on said front surface of said liquid impermeable backing for sealing said assay strip to said liquid impermeable backing at a bottom and two sides of said assay strip; and
   a rear cover means provided on said rear surface of said liquid impermeable backing for sealing said wicking means to said liquid impermeable backing at two sides of said wicking means.

3. An assay assembly according to claim 2, wherein said rear cover is injected molded and said backing and front and rear cover are made from resilient materials.

4. A method for in field urine analysis comprising the steps of:

introducing a urine sample into a transparent container having an opening after removing a cover from said opening, said transparent container further being provided with an assay assembly for chemically analyzing said urine sample, said assay assembly comprising:

a liquid impermeable backing;

at least one assay strip provided on a front surface of said liquid impermeable backing facing outwardly and viewable through said transparent container means;

a wicking means provided on a rear surface of said liquid impermeable backing separated from said assay strip by said liquid impermeable backing with one portion of said wicking means extending over a top edge of said liquid impermeable backing and overlapping said assay strip;

a front cover means provided on said front surface of said liquid impermeable backing for sealing said assay strip to said liquid impermeable backing at a bottom and two sides of said assay strip; and placing the cover means back on the container means to seal the opening; and allowing the urine to wick up the wicking means over the top edge of said liquid impermeable backing and down the portion of the wicking means to the assay strip to react with the assay strip.

5. An assaying device for in field urinalysis comprising:

a transparent container means having an opening for collecting a urine sample therein;

a cover means for sealing said opening of said container means; and an assay assembly provided in said transparent container means for chemically analyzing said urine sample, said assay assembly comprising:

a liquid impermeable layer;

at least one assay strip provided on a front surface of said liquid impermeable layer facing outwardly and viewable through said transparent container means;

at least one longitudinally extending wicking means provided on a back surface of said liquid impermeable layer separated from said assay strip by said liquid impermeable layer with one portion of said wicking means extending over a top edge of said liquid impermeable layer with said portion of said wicking means overlapping said assay strip; and a cover means provided on said assay strip and wicking means for sealing said wicking means and assay strip from liquid contact with said urine sample except at one end portion of said wicking means.

6. A method for in field urinalysis comprising the steps of;

introducing a urine sample into a transparent container having an opening after removing a cover from said opening, said container further being provided with an assay assembly for chemically analyzing said urine sample, said assay assembly comprising:

a liquid impermeable layer;

at least one assay strip provided on a front surface of said liquid impermeable layer facing oddly and viewable through said transparent container means;

at least one longitudinally extending wicking means provided on said liquid impermeable layer separated from said assay strip by said liquid impermeable layer with one portion of said wicking means extending over a top edge of said liquid impermeable backing and overlapping said assay strip;

a cover means provided on said assay strip and wicking means for sealing said wicking means and assay strip from liquid contact with said urine sample except at a bottom portion of said wicking means;

placing the cover means back on the container to seal the opening; and allowing the urine to wick up the wicking means and down the assay strip to react with the assay strip.

* * * * *